United States Patent [19]

Malamas

[11] Patent Number: 5,189,044

[45] Date of Patent: *Feb. 23, 1993

[54] ISOQUINOLINE-1,3-DIONE ACETYL CARBAMATES USEFUL AS ALDOSE REDUCTASE INHIBITORS

[75] Inventor: Michael S. Malamas, Jamison, Pa.

[73] Assignee: American Home Products Corporation, New York, N.Y.

[*] Notice: The portion of the term of this patent subsequent to Jan. 8, 2008 has been disclaimed.

[21] Appl. No.: 854,196

[22] Filed: Mar. 20, 1992

[51] Int. Cl.$^5$ .................. A61K 31/44; C07D 417/14
[52] U.S. Cl. .................................... 514/309; 546/142
[58] Field of Search .................... 546/142; 514/309

[56] References Cited

U.S. PATENT DOCUMENTS 5,037,831  8/1991  Malamas ............................. 546/18
5,045,544  9/1991  Malamas ............................. 514/278

Primary Examiner—Alan L. Rotman
Assistant Examiner—Zinna N. Davis
Attorney, Agent, or Firm—Walter Patton

[57] ABSTRACT

This invention relates to isoquinoline-1,3-dione acetyl carbamates and their pharmaceutically acceptable salts thereof, to processes for their preparation, to methods for using the compounds, and to pharmaceutical preparations thereof. The compounds have pharmaceutical properties which render them beneficial for the treatment of diabetes mellitus complications and associated conditions.

4 Claims, No Drawings

ISOQUINOLINE-1,3-DIONE ACETYL CARBAMATES USEFUL AS ALDOSE REDUCTASE INHIBITORS

BACKGROUND OF THE INVENTION

This invention relates to isoquinoline-1,3-dione acetyl carbamates and their pharmaceutically acceptable salts thereof, to processes for their preparation, to methods for using the compounds, and to pharmaceutical preparations thereof. The compounds have pharmaceutical properties which render them beneficial for the treatment of diabetes mellitus and associated conditions.

The use of insulin and/or oral hypoglycemic agents in the treatment of diabetes mellitus has prolonged the life of many of these patients. However, their use has not had a demonstrable impact on the development of diabetic complications such as neuropathy, nephropathy, retinopathy, cataracts and vascular disease which accompany the underlying metabolic disorder. There is little question that chronic hyperglycemia plays a major role in the genesis of these complications, and that complete normalization of blood glucose would likely prevent most if not all complications. For a number of reasons, though, chronic normalization of blood glucose has not been achieved with the currently available therapies. The development of diabetic complications has recently been linked to the increased accumulation of tissue sorbitol resulting from chronic hyperglycemia. Therapeutic reduction of sorbitol accumulation could potentially prevent the development of diabetic complications.

In mammals, including humans, the key enzyme involved in the conversion of hexoses to polyols (e.g. the sorbitol pathway) is aldose reductase. J. H. Kinoshita and collaborators [see J. H. Kinoshita et al., Biochem. Biophys. Acta, 158,472(1968) and references cited therein] have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nerves and kidney of diabetic animals, [see A. Pirie and R. van Heyningen, Exp. Eye Res., 3, 124 (1964); L. T. Chylack and J. H. Kinoshita, Invest. Ophthal., 8, 401 (1969) and J. D. Ward and R. W. D. Baker, Diabetol., 6, 531 (1970)].

SUMMARY OF THE INVENTION

The isoquinoline-1,3-dione acetyl carbamates of the present invention are represented by formula (I):

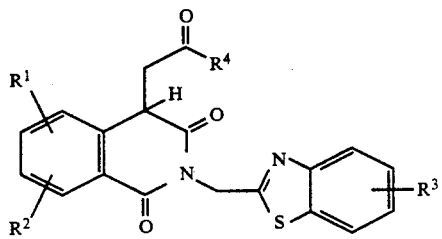

wherein:

$R^1$, $R^2$, and $R^3$ are independently hydrogen, alkyl containing 1 to 6 carbon atoms, halogen, lower alkoxy containing 1 to 6 carbon atoms, trifluoromethyl and nitro; $R^4$ is lower alkyl carbamate wherein lower alkyl contains 1 to 6 carbon atoms, aryl carbamate and aryl (lower alkyl) carbamate wherein aryl contains 6 to 10 carbon atoms and lower alkyl contains 1 to 6 carbon atoms; and the pharmaceutically acceptable salt thereof.

A more preferred group of compounds of the present invention is represented by formula (II):

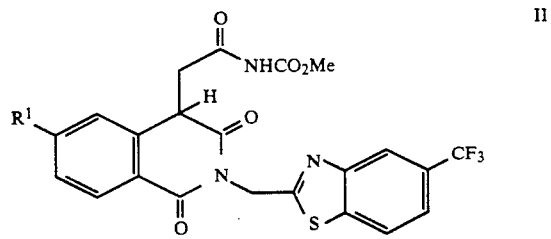

wherein: $R^1$ is hydrogen or halogen; and the pharmaceutically acceptable salt thereof. The most preferred compounds of the present invention are set forth below:

[[1,2,3,4-tetrahydro-1,3-dioxo-2-[[5-(trifluoromethyl)-2-benzothiazolyl]methyl]-4-isoquinolinyl]acetyl]carbamic acid methyl ester; and

[[6-fluoro-1,2,3,4-tetrahydro-1,3-dioxo-2-[[5-(trifluoromethyl)-2-benzothiazolyl]methyl]-4-isoquinolinyl]acetyl]carbamic acid methyl ester and the pharmaceutically acceptable salt thereof.

PRIOR ART

U.S. Pat. No. 4,983,613, Jan. 8, 1991 which discloses the isoquinoline acetic acids and acetyl carbamates of formula:

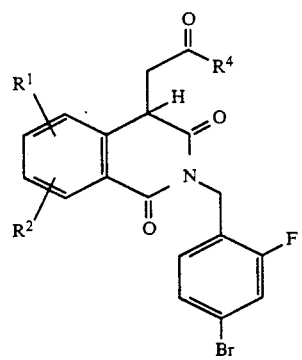

wherein:

$R^1$ and $R^2$ are independently hydrogen, alkyl containing 1 to 6 carbon atoms, halogen, or trifluoromethyl; and $R^4$ is hydroxy, lower alkyl carbamate, aryl carbamate or aryl (lower alkyl) carbamate.

DETAILED DESCRIPTION OF THE INVENTION

The isoquinoline-1,3-dione acetyl carbamates of this invention may be administered to mammals, for example, man, cattle or rabbits, either alone or in dosage forms, i.e., capsules or tablets, combined with pharmacologically acceptable excipients.

The compounds of this invention may be given orally. However, the method of administering the present active ingredients of this invention is not to be construed as limited to a particular mode of administration.

For example, the compounds may be administered topically directly to the eye in the form of drops of sterile, buffered ophthalmic solutions, preferably of pH 7.2-7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2-7.6, containing a pharmaceutically acceptable buffer.

The dosage of the isoquinoline-1,3-dione acetyl carbamates will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects. For topical administration, a 0.05-1.0% solution may be administered dropwise in the eye. The frequency of instillation varies with the subject under treatment from a drop every two or three days to once daily. For oral or parenteral administration a preferred level of dosage ranges from about 50 mg to about 250 mg per kilo of body weight per day, although aforementioned variations will occur. However, a dosage level that is in the range from about 50 mg to 100 mg per kilo of body weight per day is most satisfactory.

Unit dosage forms such as capsules, tablets, pills and the like may contain from about 50 mg to about 500 mg of the active ingredients of this invention with a pharmaceutical carrier. Thus, for oral administration, capsules can contain from between about 50 mg to about 500 mg of the active ingredients of this invention with or without a pharmaceutical diluent. Tablets, either effervescent or noneffervescent, can contain between about 50 to 500 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents, for example, magnesium stearate.

The isoquinoline-1,3-dione acetyl carbamates also can be used in combination with insulin or oral hypoglycemic agents to produce a beneficial effect in the treatment of diabetes mellitus. In this instance, commercially available insulin preparations or oral hypoglycemic agents, exemplified by acetohexamide, chloropropamide, tolazamide, tolbutamide and phenformin, are suitable. The compounds herein can be administered sequentially or simultaneously with insulin or the oral hypoglycemic agent. Suitable methods of administration, compositions and doses of the insulin preparation or oral hypoglycemic agent are described in medical textbooks; for instance, *Physicians' Desk Reference*, 42 ed., Medical Economics Co., Oradell, N.J., U.S.A., 1988.

The aldose reductase inhibiting property of the compounds of this invention and the utilization of the compounds in preventing, diminishing and alleviating diabetic complications are demonstrable in experiments using galactosemic rats, see Dvornik et al., Science, 182, 1146 (1973). Such experiments are exemplified hereinbelow after the listing of the following general comments pertaining to these experiments:

(a) Four or more groups of six male rats, 50-70 g, Sprague-Dawley strain, were used. The first group, the control group, was fed a mixture of laboratory chow (Rodent Laboratory Chow, Purina) and glucose at 20% (w/w %) concentration. The untreated galactosemic group was fed a similar diet in which galactose is substituted for glucose. The third group was fed a diet prepared by mixing a given amount of the test compound with the galactose containing diet. The concentration of the galactose in the diet of the treated groups was the same as that for the untreated galactosemic group.

(b) After four days, the animals were killed by euthanization. The lenses were removed from the eyes and weighed. The sciatic nerves were dissected as completely as possible and weighed. Both tissues when frozen can be kept up to two weeks before being analyzed for dulcitol.

(c) The polyol determination was performed by a modification of the procedure of M. Kraml and L. Cosyns, Clin. Biochem., 2,373 (1969). Only two minor reagent changes were made: (a) The rinsing mixture was an aqueous 5% (w/v) trichloroacetic acid solution and (b) the stock solution was prepared by dissolving 25 mg of dulcitol in 100 ml of an aqueous trichloroacetic acid solution. [N.B.: For each experiment the average value found in the tissue from rats fed the glucose diet was subtracted from the individual values found in the corresponding tissue in galactose-fed rats to obtain the amount of polyol accumulated.] The aldose reductase inhibiting effects of the compounds of formula (I) were also tested by employing an in vitro testing procedure similar to that described by S. Hayman and J. H. Kinoshita, J. Biol. Chem., 240,877 (1965). In the present case the procedure of Hayman and Kinoshita was modified in that the final chromatography step was omitted in the preparation of the enzyme from bovine lens.

The following tabulated results show that the isoquinoline-1,3-dione acetyl carbamates of this invention show the property that they are active both in vitro and in vivo and diminish the accumulation of dulcitol in the sciatic nerves and diaphragms of rats fed galactose. The figures under N and D represent the percentage decrease of dulcitol accumulation in the tissues of the sciatic nerve and diaphragm, respectively, for treated rats as compared to untreated rats.

Aldose Reductase Inhibitors

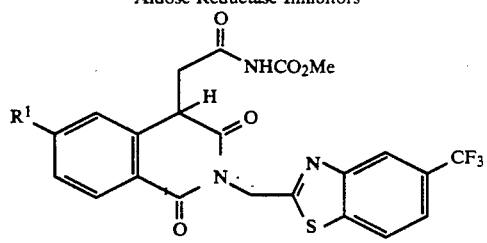

| $R^1$ | % Inhibition in vitro | Dose mg/kg/day | % Lowering Galacitol Accumulation in Vivo | |
|---|---|---|---|---|
| | | | Sciatic Nerve | Diaphragm |
| H | 95($10^{-5}$ M) | 48.8 | 61 | 81 |
| | | 96.6 | 73 | 87 |
| F | 83($10^{-5}$ M) | 93.6 | 59 | 81 |

| -continued | | |
|---|---|---|
| 49.3 | 39 | 74 |
The process: The isoquinoline-1,3-dione acetyl carbamates of the present invention were prepared by the following synthetic scheme.
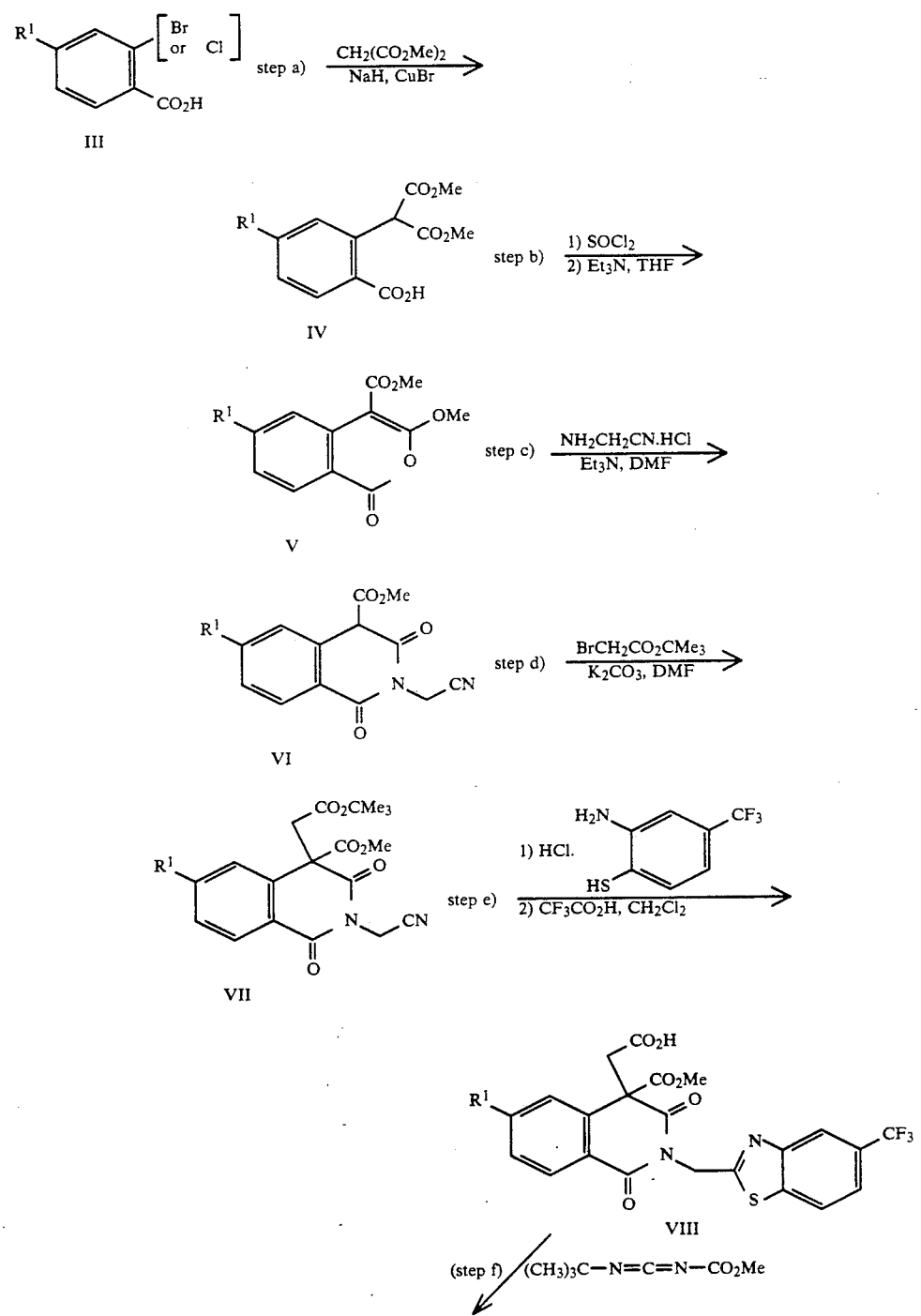

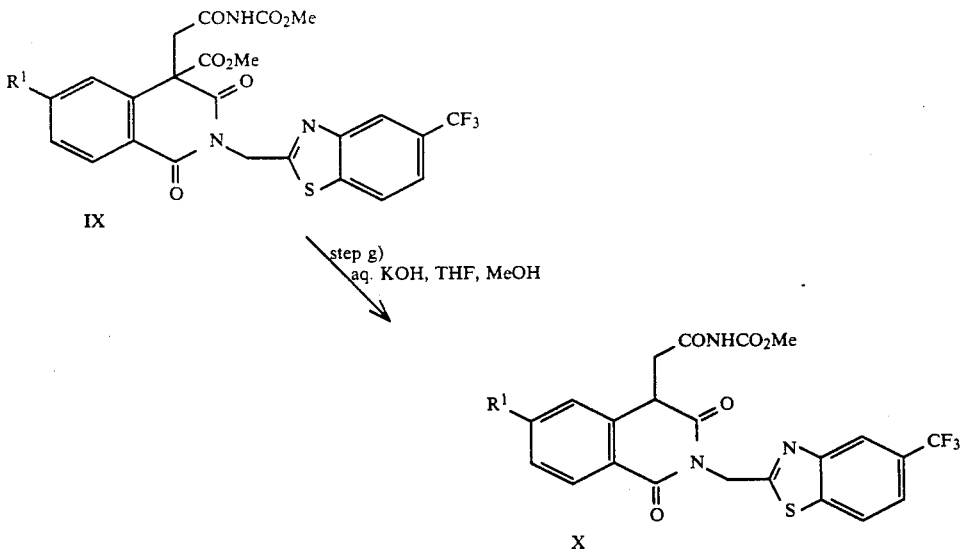

wherein $R^1$ is as defined above

Step a) Reacting either 2-bromobenzoic acid or 2-chlorobenzoic acid of formula (III) wherein $R^1$ is as defined above with dimethyl malonate and NaH in the presence of a catalytic amount of CuBr to produce the propanedioic acid dimethyl ester of formula (IV) wherein $R^1$ is as defined above.

The 2-bromobenzoic acids or 2-chlorobenzoic acids of formula (III) required for the present invention are commercially available compounds or can be prepared by known methods.

Step b) The propanedioic acid dimethyl ester of formula (IV) can be reacted with thionyl chloride under refluxing conditions to produce the corresponding acid chloride which upon treatment with $Et_3N$ in a conventional solvent which does not adversely influence the reaction, for example, tetrahydrofuran, can produce the compound of formula (V), wherein $R^1$ is as defined above.

Step c) The compound of formula (V), wherein $R^1$ is as defined above, is reacted with $NH_2CH_2CN \cdot HCl$ in the presence of $Et_3N$ in a conventional solvent which does not adversely influence the reaction, for example, DMF, produces the compound of the formula (VI), wherein $R^1$ is as defined above.

Step d) The compound of formula (VI), wherein $R^1$ is as defined above, is reacted with an inorganic base such as potassium carbonate in a conventional solvent which does not adversely influence the reaction, for example, N,N-dimethylformamide and subsequent addition of the tert-butyl bromoacetate produces the compound of formula (VII), wherein $R^1$ is as defined above.

Step e) The compound of formula (VII), wherein $R^1$ is as defined above, can be reacted with 3-amino-4-mercaptobenzotrifluoride hydrochloride and an organic acid such as trifluoroacetic acid in a conventional solvent which does not adversely influence the reaction, for example, methylene chloride, to produce the compound of formula (VIII), wherein $R^1$ is as defined above.

Step f) The compound of formula (VIII), wherein $R^1$ is as defined above, can be reacted with N-methoxycarbonyl-N'-tert-butylcarbodiimide in a conventional solvent which does not adversely influence the reaction, for example, tetrahydrofuran, to produce the compound of formula (IX), wherein $R^1$ is as defined above.

Step g) The compound of formula (IX), wherein $R^1$ is as defined above, can be reacted with an aqueous inorganic base, such as potassium hydroxide in an alcohol-THF solution, to produce the compound of formula (X), wherein $R^1$ is as defined above.

The chemical bases which are used as reagents in this invention to prepare the aforementioned pharmaceutically acceptable salts are those which form nontoxic salts with the various herein described acidic isoquinoline acetic acids and acetyl carbamates. These particular non-toxic base salts are of such a nature that their cations are said to be essentially nontoxic in character over the wide range of dosage administered. Examples of such cations include those of sodium, potassium, calcium, and magnesium. These salts can easily be prepared by simply treating the aforementioned acidic isoquinoline-1,3-dione acetyl carbamates with an aqueous solution of the desired pharmacologically acceptable cation and then isolating by filtration or evaporation the resulting salts.

Alternatively, they may also be prepared by mixing organic solutions of the said acidic compounds and the desired alkali metal hydride together and then isolating the resulting salts by precipitation in non-polar solvent. In either case, stoichiometric quantities of reagents must be employed in order to ensure completeness of reaction and maximum production yields with respect to the desired final product.

The following Examples further illustrate this invention.

EXAMPLE 1

1,2,3,4-Tetrahydro-1,3-dioxo-2-[[5-(trifluoromethyl)-2-benzothiazolyl]
methyl]-4-isoquinolinyl]acetyl]carbamic acid methyl esther Step a)

(2-Carboxyphenyl)propanedioic acid dimethyl ester

To a rapidly stirred cold suspension (0° C.) of 2-bromobenzoic acid (30.0 g, 149.32 mmol), cuprous bromide (2.14 g, 14.93 mmol) and dimethyl malonate (300 mL) was added NaH (80% in mineral oil, 10.75 g, 358.37 mmol) over a 30 minute period, while a stream of dry N$_2$ was passed over the mixture. After the addition of the NaH had been completed, the mixture was stirred for 10 minutes at room temperature and 30 minutes at 70° C. (external oil bath temperature). At this point, the suspension had turned to a solid mass, which was dissolved in H$_2$O (1000 mL). The aqueous layer was extracted with diethyl ether (3×500 mL) and was acidified with HCl (2N). The mixture was extracted with EtOAc and dried over MgSO$_4$. Evaporation gave an off-white solid which was recrystallized from Et$_2$O/hexane (after cooling to −20° C.) to give a white solid (34.2 g, 90.9%); M.P. 119°-120° C.

IR (KBr, cm$^{-1}$): 3300-2700 (CO$_2$H), 1750 (CO), 1730 (CO), 1680 (CO);

$^1$H NMR (DMSO-d$_6$, 400 MHz): δ 3.67 [s, 6H, -CH(CO$_2$CH$_3$)$_2$], 5.72 [s, 1H, -CH(CO$_2$CH$_3$)$_2$], 7.3 (d, J=7.76 Hz, 1H, Ar-H), 7.45 (dt, J=7.66 Hz, 1.12 Hz, 1H, Ar—H), 7.6 (dt, J=7.66 Hz, 1.45 Hz, 1H, Ar—H), 7.94 (dd, J=7.8 Hz, 1.33 Hz, 1H, Ar—H), 13.2 (s, 1H, —CO$_2$H);

MS (m/e): 252 (M+), 220 (M+ —CH$_3$OH), 188 (M+ —2×CH$_3$OH).

Anal. Calcd.: C, 57.14; H, 4.80;
Found: C, 57.05; H; 4.78.

The following compounds were prepared in substantially the same manner as that of Example 1, Step a):

(2-Carboxy-6-fluorophenyl)propanedioic acid dimethyl ester

IR (KBr, cm$^{-1}$): 3400-2700 (CO$_2$H), 1730 (CO), 1680 (CO);

$^1$H NMR (DMSO-d$_6$, 400 MHz): δ 3.68 [s, 6H, (-CO$_2$Me)$_2$], 5.79 [s, 1H, Ar—CH(CO$_2$Me)$_2$], 7.12 (dd, J=10.06 Hz, 2.61 Hz, 1H, Ar—H), 7.33 (dt, J=8.48 Hz, 2.64 Hz, 1H, Ar—H), 8.03 (dd, 8.77 Hz, 6.17 Hz, 1H, Ar—H); MS (m/e): 270 (M+), 238 (M+ —CH$_3$OH), 210 (M+ —CH$_3$OH, —CO), 151 (M+ —CH$_3$OH, —CO, —CO$_2$CH$_3$). M.P. 121.5°-123.0° C.

Anal.Calcd.: C, 53.34; H, 4.10.
Found: C, 53.36; H, 3.93.

Step b)

3-Methoxy-1-oxo-1H-2-benzopyran-4-carboxylic acid methyl ester

A mixture of (2-carboxyphenyl)propanedioic acid dimethyl ester (10.09 g, 39.68 mmol) and SOCl$_2$ (100 g) was refluxed for 2 hours. The volatiles were removed in vacuo and the crude product (acid chloride) was dissolved in THF (20 mL). Triethylamine (27.64 mL, 198.4 mmol) was added and the mixture was stirred for 30 minutes. The yellowish suspension was poured into HCl (1N, 1000 mL), extracted with EtOAc and the organic extracts were dried over MgSO$_4$. Evaporation and crystallization from acetone/ether/hexane (at −20° C.) gave a white solid (87.6 g, 94.4%); M.P. 129°-130° C.

IR (KBr, cm$^{-1}$): 1740 (C=O), 1685 (C=O); MS (m/e): 234 (16, M+), 206 (38.5, M+ —CO), 203 (12, M+ —OMe);

$^1$H NMR (DMSO-d$_6$, 400 MHz): d (3.82, (s, 3H, -CO$_2$Me), 4.03 (s, 3H, -OMe), 7.42 (t, J=7.26 Hz, 1H, Ar-H), 7.8 (t, J=8.2 Hz, 1H, Ar-H), 7.9 (d, J=8.3 Hz, 1H, Ar-H), 8.1 (d, J=7.26 Hz, 1H, Ar-H);

Anal. Calcd.: C, 61.59; H, 4.30;
Found: C, 61.82; H, 4.29

The following compound was prepared in substantially the same manner as that of Example 1 Step b):

6-Fluoro-3-methoxy-1-oxo-1H-2-benzopyran-4-carboxylic acid methyl ester

IR (KBr, cm$^{-1}$): 1750(C=O), 1685 (C=O); MS (m/e): 252 (24, M+), 224 (54, M+ —CO);

$^1$H NMR (DMSO-d$_6$, 400 MHz): d 3.81 (s, 3H, —CO$_2$CH$_3$), 4.06 (s, 3H, —OCH3—), 7.27 (dt, J=8.3 Hz, 1H, Ar—H), 7.8 (dd, J=11.83 Hz, 2.49 Hz, 1H, Ar—H), 8.16 (dd, J=8.92 Hz, 6.2 Hz, 1H, Ar—H);

M.P. 142°-143° C.

Anal. Calcd.: C, 57.15; H, 3.60;
Found: C, 57.19; H, 3.57.

Step c)

2-(Cyanomethyl)-1,2,3,4-tetrahydro-1,3-dioxo-4-isoquinolinecarboxylic acid methyl ester To a solution of 3-methoxy-1-oxo-1H-2-benzopyran-4-carboxylic acid methyl ester (8.09, 34.19 mmol) in DMF (100 mL) was added aminoacetonitrile hydrochloride (6.32 g, 68.37 mmol) and the suspension was stirred until all the materials have dissolved. Triethylamine (14.3 mL, 102.57 mmol) was added and the mixture was stirred at 100° C. for 30 minutes, and then poured into H$_2$O, acidified with HCl (2N) and extracted with EtOAc. The organic extracts were dried over MgSO$_4$. Evaporation and crystallization from acetone/ether/hexane (at −20° C.) gave a yellowish solid (6.5 g, 73.7%); M.P. 169°-171° C.

IR (KBr, cm$^{-1}$): 3400 (OH), 1670 (C=O);

$^1$H NMR (DMSO-d$_6$, 400 MHz): d (3.7, 3.98, s, 3H, —CO$_2$CH$_3$, rotameric), (4.92, 5.44, s, 2H, —NCH$_2$CN, rotameric), 7.2-8.4 (m, 4H, Ar—H, rotomeric; MS(m/e): 258 (20, M+), 226 (43, M+ —MeOH), 199 (13, M+ —CO$_2$Me).

Anal. Calcd: C, 60.47; H, 3.90; N, 10.85;
Found: C, 60.27; H, 3.77; N, 10.69.

The following compound was prepared in substantially the same manner as that of Example 1, step c)

2-(Cyanomethyl)-6-fluoro-1,2,3,4-tetrahydro-1,3-dioxo-4-isoquinolinecarboxylic acid methyl ester Anal. Calcd.: C, 56.53; H, 3.28; N, 10.14
Found: C, 56.45; H, 3.22; N, 10.13.
M.P.178°-179° C.

Step d)

2-(Cyanomethyl)-1,2,3,4-tetrahydro-4-(methoxycarbonyl)-1,3-dioxo4-isoquinolineacetic acid 1,1-dimethylethyl ester To a suspension of 2-(cyanomethyl)-1,2,3,4-tetrahydro-1,3-dioxo-4-isoquinoline carboxylic acid methyl ester (6.5 g, 25.19 mmol), K$_2$CO$_3$ (6.95 g, 50.38 mmol) and anhydrous DMF (100 mL) was added tert-butyl bromoacetate (6.1 mL, 37.79 mmol). After stirring at 85° C. for 3 hours, the mixture was poured into H$_2$O, acidified with HCl (2N) and extracted with EtOAc. The organic extracts were dried over MgSO$_4$. Evaporation and purification by flash chromatography on silica gel (hexane/EtOAC 4/1) gave a white solid (8.5 g, 90.7%); M.P. 48°-50° C.

IR (KBr, cm$^{-1}$): 1745 (C=O), 1730 (C=O), 1670 (C=O); MS (CI): 373 (38, M+ +H), 317 (100, M+ +H,-CMe$_3$);

$^1$H NMR (DMSO-d$_6$ 200 MHz): d 1.03 (s, 9H, —CO$_2$CMe$_3$), 3.58 (s, 3H, CO$_2$CH$_3$), 3.64 (s, 2H, —CH$_2$CO$_2$—), 5.05 (s, 2H, —NCH$_2$CN), 7.64 (m, 2H, Ar—H), 7.78 (dd, J=7.4 Hz, 2.0 Hz, 1H, Ar—H), 8.24 (dd, J=8.2 Hz, 1.6 Hz, 1H, Ar—H);.

Anal. Calcd: C, 61.28; H, 5.41; N, 7.52;
Found: C, 61.61; H, 5.49; N, 7.13.

The following compound was obtained in substantially the same manner as that of Example 1, Step d)

2-(Cyanomethyl)-6-fluoro-1,2,3,4-tetrahydro-4-(methoxycarbonyl)-1,3-dioxo-4-isoqinolineacetic acid 1,1-dimethylethyl ester Anal. Calcd: C, 58.46; H, 4.91; N, 7.18
Found: C, 58.65; H, 4.98; N, 7.08.
M.P.133°-135° C.

Step e)

1,2,3,4-Tetrahydro-4-(methoxycarbonyl)-1,3-dioxo-2-[[(5-trifluoromethyl)-2-benzothiazolyl]methyl]-4-isoquinolineacetic acid To a mixture of 3-amino-4-mercaptobenzotrifluoride hydrochloride (6.1 g, 26.2 mmol) and EtOH (150 mL) was added Et$_3$N (3.65 mL). After stirring for 10 minutes, 2-(cyanomethyl)-1,2,3,4-tetrahydro-4-(methoxycarbonyl)-1,3-dioxo-4-isoquinolineacetic acid 1,1-dimethylethyl ester (6.5 g, 17.47 mmol) was added and the mixture was refluxed for 15 hours, poured into H$_2$O, acidified with HCl (2N) and extracted with EtOAc. The organic extracts were dried over MgSO$_4$. Evaporation gave an oil (9.6 g) which was dissolved in CH$_2$Cl$_2$ (80 mL). Trifluoroacetic acid (20 mL) was added and the mixture was stirred at room temperature for 8 hours. The volatiles were removed in vacuo and the residue was purified by flash chromatography on acid washed (5%,H$_3$PO$_4$ in MeOH) silica gel to give a white solid (6.3 g, 73.3%); M.P.199°-201° C.

IR (KBr, cm$^{-1}$): 3200-2500 (CO$_2$H), 1750 (C=O), 1710 (C=O), 1670 (C=O);

$^1$H NMR (DMSO-d$_6$, 400 MHz) d 3.57 (s, 3H, —CO$_2$CH$_3$), 3.68 (dd, J=17.85 Hz, 2H, —CH$_2$CO$_2$H), 5.61 (s, 2H, —NCH$_2$—), 7.62 (m, 2H, Ar—H), 7.81 (m, 2H, Ar—H), 8.2 (dd, J=7.9 Hz, 1.04 Hz, 1H, Ar—H), 8.33 (dd, J=8.5 Hz, 0.92 Hz, 1H, Ar—H), 8.34 (d, J=083 Hz, 1H, Ar—H). MS(m/e): 492 (6, M$^{30}$), 448 (6, M$^+$—CO2), 416 (62, M$^+$—CO$_2$—MeOH).

Anal. Calcd: C, 53.66; H, 3.07; N, 5.69;
Found: C, 53.40; H, 3.01; N, 5.54.

The following compound was prepared in substantially the same manner as that of Example 1, step e).

6-Fluoro-1,2,3,4-tetrahydro-4-(methoxycarbonyl)-1,3-dioxo-2-[[(5-trifluoromethyl)-2-benzothiazolyl]methyl]-4-isoquinolineacetic acid Anal. Calcd: C, 51.77; H, 2.76; N, 5.49;
Found: C, 51.62; H, 2.97; N, 5.18
M.P. 177°-179° C.

Step f)

[[1,2,3,4-Tetrahydro-4-(methoxycarbonyl)1,3-dioxo-2-[[(5-(trifluoromethyl)-2-benzothiazolyl]methyl]-4-isoquinolinyl]-acetyl]carbamic acid methyl ester To a solution of 1,2,3,4-tetrahydro-4-(methoxycarbonyl)-1,3-dioxo-2-[[(5-trifluoromethyl)-2-benzothiazolyl]methyl]-4-isoquinolineacetic acid (1.93 g, 3.92 mmol) and anhydrous THF (20 mL) was added N-methoxycarbonylN'-tert-butylcarbodiimide (734 mg, 4.7 mmol), and the mixture was refluxed for 8 hours. The volatiles were removed and the residue was purified by flash chromatography on silica gel (hexane/EtOAc 2:1) to yield a white solid (1.92 g, 89.3%); M.P. 199°-201° C.

IR (KBr, cm$^{-1}$): 3150 (NH), 1750 (C=O), 1670 (c=O); MS (m/e): 550 (20, M+H)$^+$;

$^1$H NMR (DMSO-d$_6$, 300 MHz): δ 3.57 (s, 3H, -CO$_2$CH$_2$), 3.61 (s, 3H, —CO$_2$CH$_3$), 3.9 (d, J=17.2 Hz, 1H, —HCHCO—), 4.1 (d, J=17.2 Hz, —HCHCO—), 5.61 (dd, J=15.5 Hz, 2H, —NCH$_2$—), 7.6 (m, 2H, Ar—H), 7.8 (m, 2H, Ar—H), 8.2 (d, J=7.4 Hz, 1H, Ar—H), 8.34 (m, 2H, Ar—H), 10.78 (s, 1H, —CONHCO$_2$Me);

Anal. Calcd: C, 52.46; H, 3.30; N, 7.65
Found: C, 52.26; H, 3.30; N, 7.53

The following compound was obtained in substantially the same manner as that of Example 1, Step f).

[[6-Fluoro-1,2,3,4-tetrahydro-4-(methoxycarbonyl)-1,3-dioxo-2-[[(5-trifluoromethyl)-2-benzothiazolyl]methyl]-4-isoquinolinyl]-acetyl]carbamic acid methyl ester IR (KBr, cm$^{-1}$): 3210 (NH), 1770 (C=O), 1675 (C=O); MS (m/e): 567 (M$^+$);

$^1$H NMR (DMSO-d$_6$, 300 MHz): δ 3.59 (s, 3H, —CO$_2$CH$_2$CH$_3$), 3.62 (s, 3H, —CO$_2$CH$_3$), 3.98 (d, J=17.2 Hz, 1H, —HCHCO—), 4.15 (d, J=17.2 Hz, 1H, —HCHCO—), 5.58 (dd, J=15.5 Hz, 2H, —NCH$_2$—), 7.5 (m, 2H, Ar—H), 7.77 (d, J=8.7 Hz, 1H, Ar—H), 8.3 (m, 3H, Ar—H) 10.79 (s, 1H, —CONHCO$_2$Me); M.P. 180°-181° C.

Anal. Calcd: C, 50,80; H, 3.02; N, 7.40
Found: C, 50.56; H, 3.22; N, 7.33

Step g)

[[1,2,3,4-Tetrahydro-1,3-dioxo-2-[[5-(trifluoromethyl)-2-benzothiazolyl]methyl]-4-isoquinolinyl]acetyl]carbamic acid methyl ester To a cold (0° C.) solution of [[1,2,3,4-tetrahydro-4-(methoxycarbonyl)-1,3-dioxo-2-[[(5-(trifluoromethyl)-2-benzothiazolyl]methyl]-4-isoquinolinyl]acetylcarbamic acid methyl ester (1.6 g, 2.91 mmol), MeOH (30 mL), THF (30 mL) and H$_2$O (3.0 mL) was added KOH (1N, 5.29 mL). After being stirred for 1 hour, the reaction mixture was poured into HCl (1N, 1000 mL), and extracted with EtOAc. The organic extracts were dried over MgSO$_4$. Evaporation and purification on acid washed silica gel (hexane/EtOAc 3:1) gave a white solid (1.1 g, 84.6%); M.P. 110°-112° C.

IR (KBr, cm$^{-1}$): 3300 (NH), 1700 (C=O), 1710 (C=O), 1670 (C=O); MS (m/e): 492 (100, M+H)$^+$;

$^1$H NMR (DMSO-d$_6$, 400 MHz): δ 3.6 (m, 5H, —CO$_2$CH$_3$, —CH$_2$CO—), 4.51 (t, J=4.15 Hz, 1H, —CHCH$_2$—), 5.5 (s, 2H, —NCH$_2$), 7.5 (m, 2H, Ar—H), 7.7 (m, 2H, Ar—H), 8.15 (dd, J=7.9 Hz, 1H, Ar—H), 8.3 (m, 2H, Ar—H), 10.7 (s, 1H, —CONHCO$_2$Me);

Anal. Calcd: C, 53.77; H, 3.28; H, 8.55
Found: C, 53.49; H, 3.36; N, 8.41

The following compound was obtained in substantially the same manner as that of Example 1, Step g)

[[6-Fluoro-1,2,3,4-tetrahydro-1,3-dioxo-2-[[5-trifluoromethyl)-2-benzothiazolyl]methyl]-4-isoquinolinyl]acetyl]carbamic acid methyl ester IR (KBr, cm$^{-1}$): 3410 (NH), 1770 (C=O); 1715 (C=O), 1670 (C=O); $^1$H NMR (DMSO-d$_6$, 400 MHz): δ 3.6 (m, 5H, —CO$_2$CH$_3$, —CH$_2$CO—), 4.52 (t, J=4.1 Hz, 1H, —CHCH$_2$—), 5.5 (s, 2H, —NH$_2$), 7.36 (dt, J=8.7 Hz, 2.28 Hz, 1H, Ar—H), 7.46 (dd, J=9.96 Hz, 1.66 Hz, 1H, Ar—H), 7.75 (dd, J=8.3 Hz, 1.24 Hz, Ar—H), 8.10 (dd, J=8.7 Hz, 6.02 Hz, 1H, Ar—H), 8.3 (m, 2H, Ar—H), 10.71 (s, 1H, —CONHCO$_2$Me); MS (m/e): 510 (M+H)$^+$; M.P. 140°-142° C.

Anal. Calcd: C, 51.87;H, 2.97; N, 8.25
Found: C, 51.52; H, 3.20; N, 8.14

We claim:

1. A compound of formula (I)

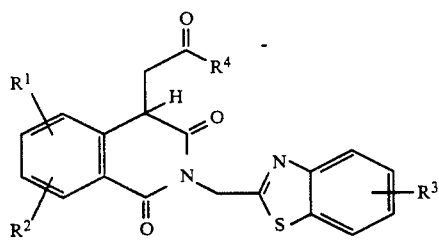

wherein:
R¹, R², and R³ are independently hydrogen, alkyl containing 1 to 6 carbon atoms, halogen, lower alkoxy containing 1 to 6 carbon atoms, trifluoromethyl and nitro; R⁴ is lower alkyl carbamate wherein lower alkyl contains 1 to 6 carbon atoms, aryl carbamate wherein aryl contains 6 to 10 carbon atoms, and aryl (lower akyl) carbamate wherein lower alkyl contains 1 to 6 carbon atoms; or a pharmaceutically acceptable salt thereof.

2. A compound according to claim 1 having the structural formula (II)

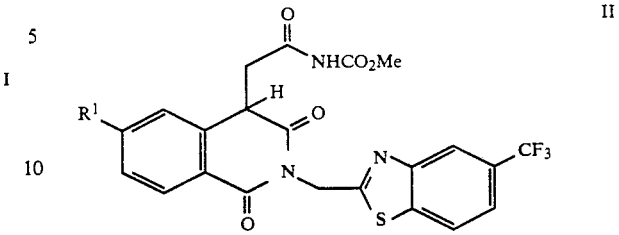

wherein: R¹ is hydrogen or halogen; or a pharmaceutically acceptable salt thereof.

3. The compound according to claim 2 designated [[1,2,3,4-tetrahydro-1,3-dioxo2-[[5-(trifluoromethyl)-2-benzothiazolyl]methyl]-4-isoquinolinyl]acetyl]carbamic acid methyl ester, or a pharmaceutically acceptable salt thereof.

4. The compound according to claim 2 designated [[6-fluoro-1,2,3,4-tetrahydro-1,3-dioxo-2-[[5-(trifluoromethyl)-2-benzothiazolyl]methyl]-4-isoquinolinyl]acetyl]carbamic acid methyl ester or a pharmaceutically acceptable salt thereof.

* * * * *

UNITED STATES PATENT AND TRADEMARK OFFICE
CERTIFICATE OF CORRECTION

PATENT NO. : 5,189,044
DATED : Feb. 23, 1993
INVENTOR(S) : Michael S. Malamas

It is certified that error appears in the above-indentified patent and that said Letters Patent is hereby corrected as shown below:

At the title page left column between lines [73] and [21] delete:

[*] Notice: The portion of the term of this patent subsequent to Jan. 8, 2008 has been disclaimed.

and insert:

[*] Notice: The portion of the term of this patent subsequent to May 22, 2007 has been disclaimed.

Signed and Sealed this

Nineteenth Day of April, 1994

Attest:

BRUCE LEHMAN

*Attesting Officer*        Commissioner of Patents and Trademarks